United States Patent
Rustad et al.

(10) Patent No.: US 8,033,292 B2
(45) Date of Patent: Oct. 11, 2011

(54) HEATED HUMIDIFIED CHAMBER WITH AUTOFEED MECHANISM

(75) Inventors: Andre Rustad, Etiwanda, CA (US); Scott Halperin, Orange, CA (US)

(73) Assignee: CareFusion 2200, Inc., San Diego, CA (US)

( * ) Notice: Subject to any disclaimer, the term of this patent is extended or adjusted under 35 U.S.C. 154(b) by 0 days.

(21) Appl. No.: 12/607,277

(22) Filed: Oct. 28, 2009

(65) Prior Publication Data

US 2010/0043886 A1    Feb. 25, 2010

Related U.S. Application Data

(63) Continuation of application No. 11/405,341, filed on Apr. 17, 2006, now Pat. No. 7,614,420.

(51) Int. Cl.
*F16K 31/28* (2006.01)
(52) U.S. Cl. .......... 137/430; 137/423; 137/428
(58) Field of Classification Search ............ 137/423, 137/426, 429, 430, 432, 433
See application file for complete search history.

(56) References Cited

U.S. PATENT DOCUMENTS

| | | | |
|---|---|---|---|
| 138,659 A * | 5/1873 | Jonson | 137/433 |
| 157,405 A * | 12/1874 | Jonson | 137/400 |
| 1,968,293 A | 7/1934 | Gould | |
| 2,603,493 A | 7/1952 | Rusconi | |
| 2,691,386 A * | 10/1954 | Madison | 137/400 |
| 2,904,062 A | 9/1959 | Techler | |
| 2,906,285 A * | 9/1959 | Rosten et al. | 137/391 |
| 3,095,005 A | 6/1963 | Thompson | |
| 3,185,302 A | 5/1965 | Kryzer | |
| 3,230,970 A | 1/1966 | Smith | |
| 5,407,604 A * | 4/1995 | Luffman | 261/4 |
| 6,031,968 A | 2/2000 | Holtmann | |
| 6,238,567 B1 | 5/2001 | Van De Moortele | |
| 6,551,504 B2 * | 4/2003 | Reed | 210/97 |
| 7,000,627 B1 * | 2/2006 | Johnson | 137/1 |

FOREIGN PATENT DOCUMENTS

| | | |
|---|---|---|
| CH | 263371 | 8/1949 |
| GB | 2382863 A | 11/2003 |

* cited by examiner

*Primary Examiner* — Stephen M Hepperle
*Assistant Examiner* — Atif Chaudry
(74) *Attorney, Agent, or Firm* — Dicke, Billig & Czaja, PLLC

(57) ABSTRACT

A heated humidifier including an autofeed mechanism disposed within a humidifier chamber. The autofeed mechanism includes a housing, a float, a stem, and a sealing body. The housing defines an inlet, an outlet, a first chamber connected to the inlet, and a second chamber connected to the outlet and the first chamber by a channel. The float moves within the second chamber with the stem projecting therefrom and through the channel. The sealing body is within the first chamber and cooperates with the stem. In an open state, the sealing body is displaced from the channel to permit filling of the humidifier chamber. In a closed state, the sealing body seals the channel to prevent liquid flow to the outlet. A location of the sealing body relative to the channel is controlled by the float as a function of a humidifier chamber liquid level.

22 Claims, 14 Drawing Sheets

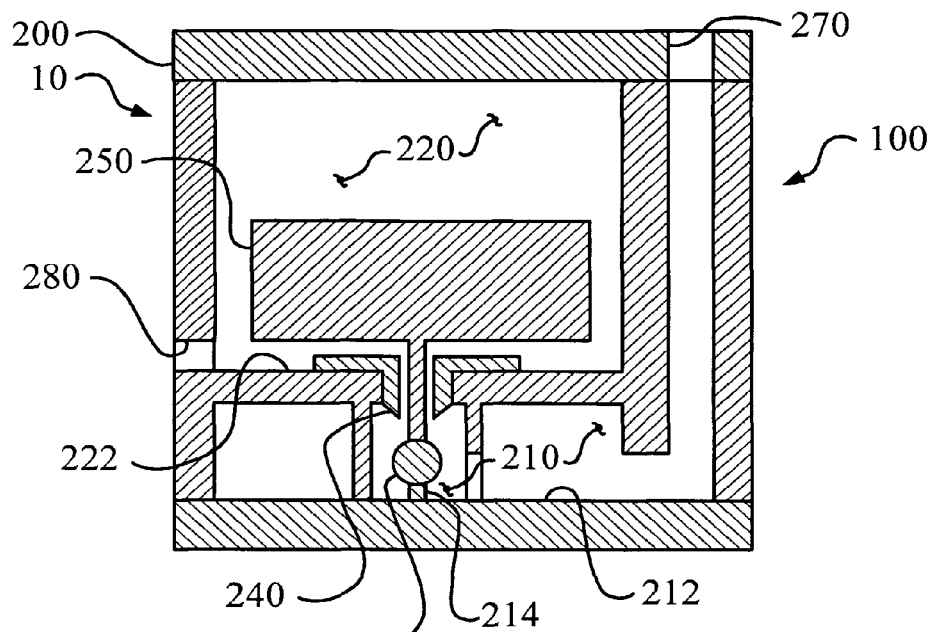
*Fig. 1*
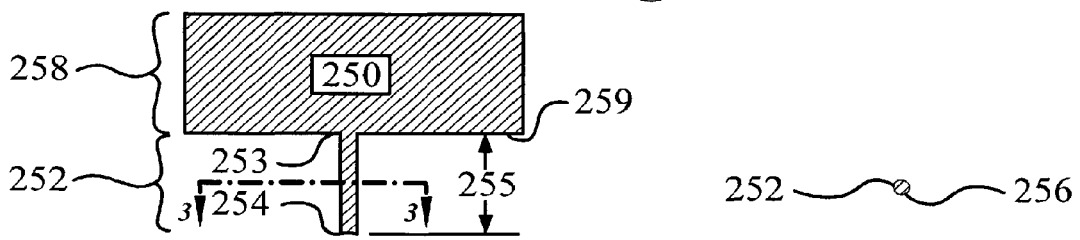
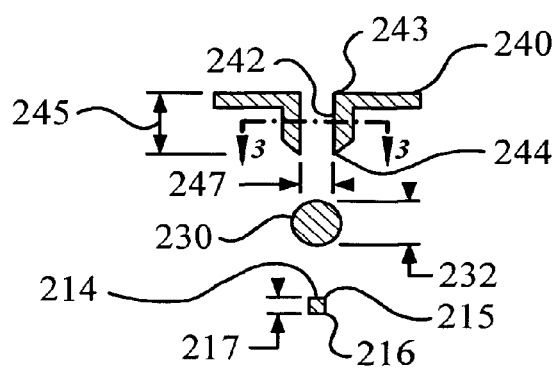
*Fig. 2*
*Fig. 3*

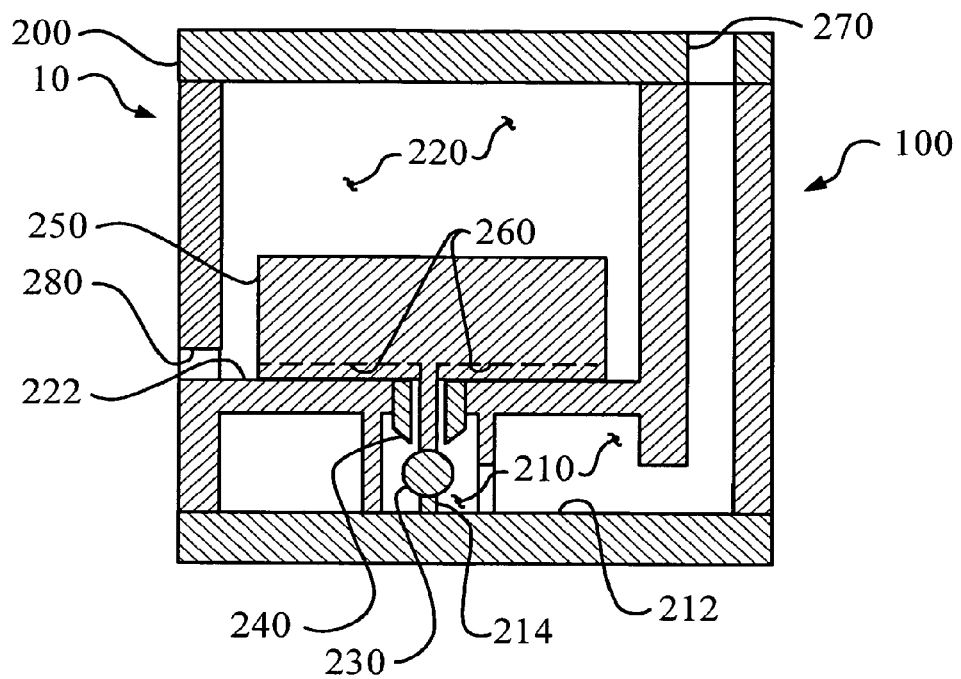
*Fig. 8*
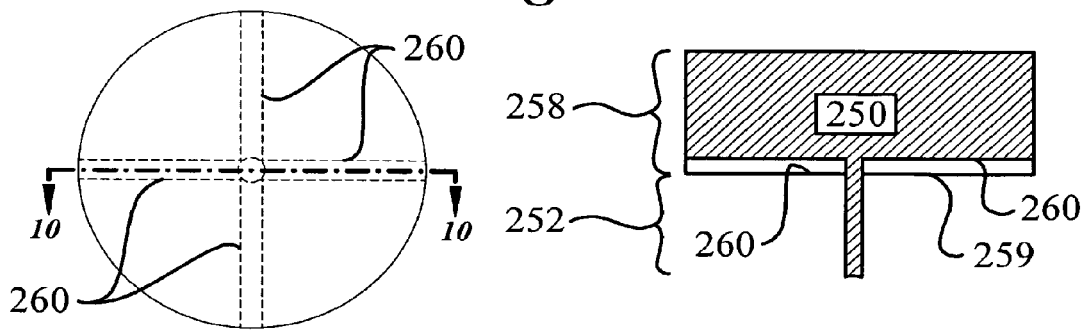
*Fig. 9*     *Fig. 10*

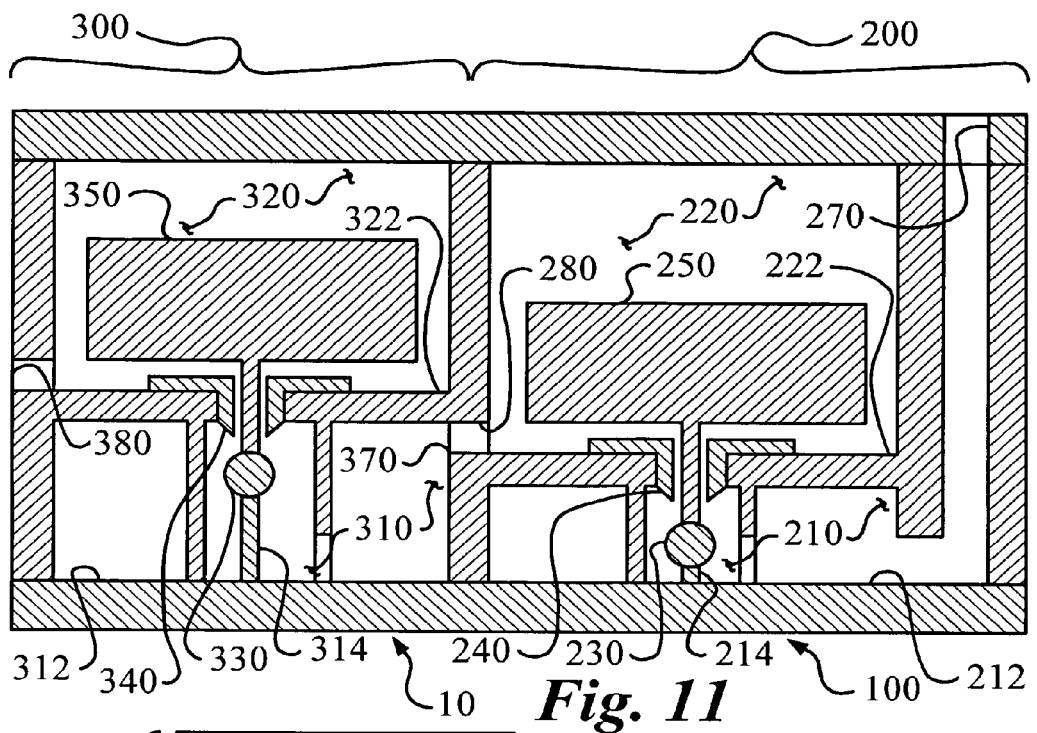
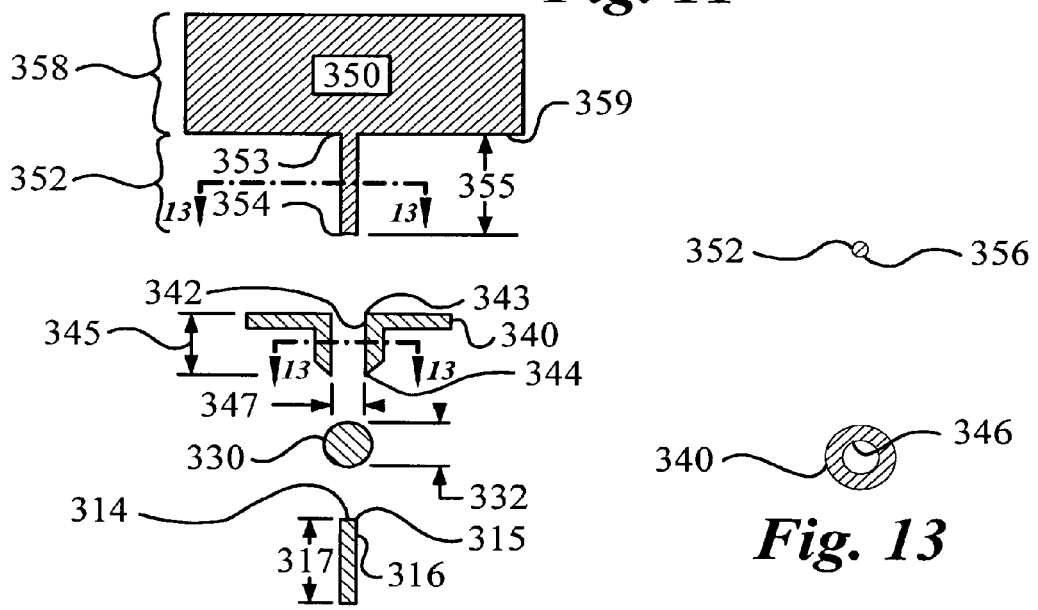
Fig. 11
Fig. 12
Fig. 13

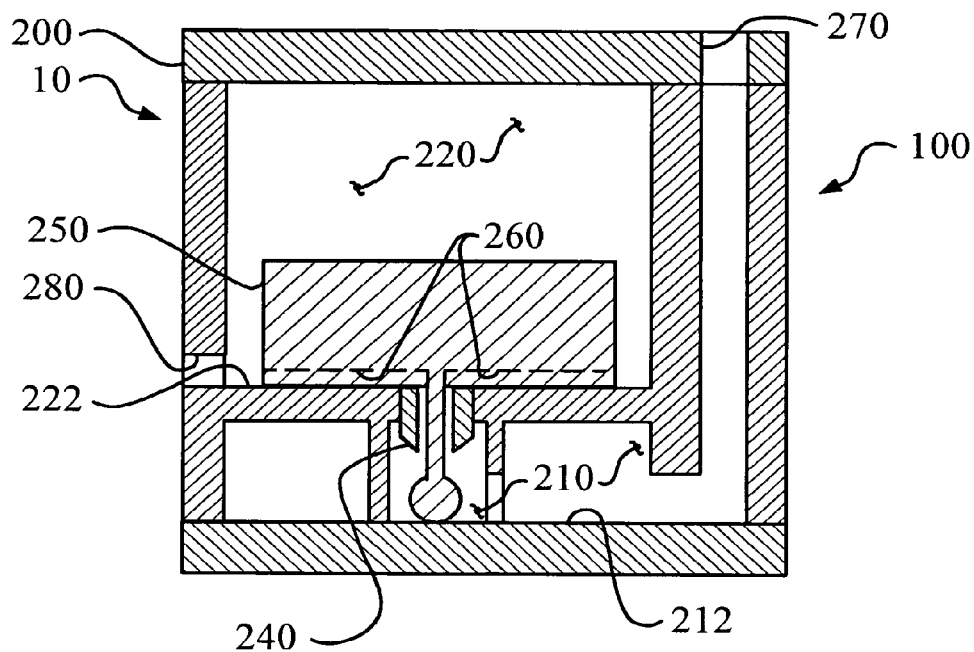
*Fig. 21*
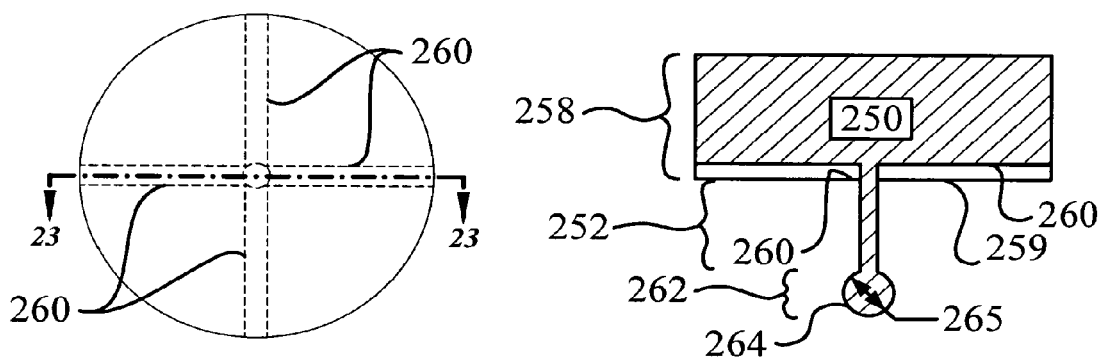
*Fig. 22*   *Fig. 23*

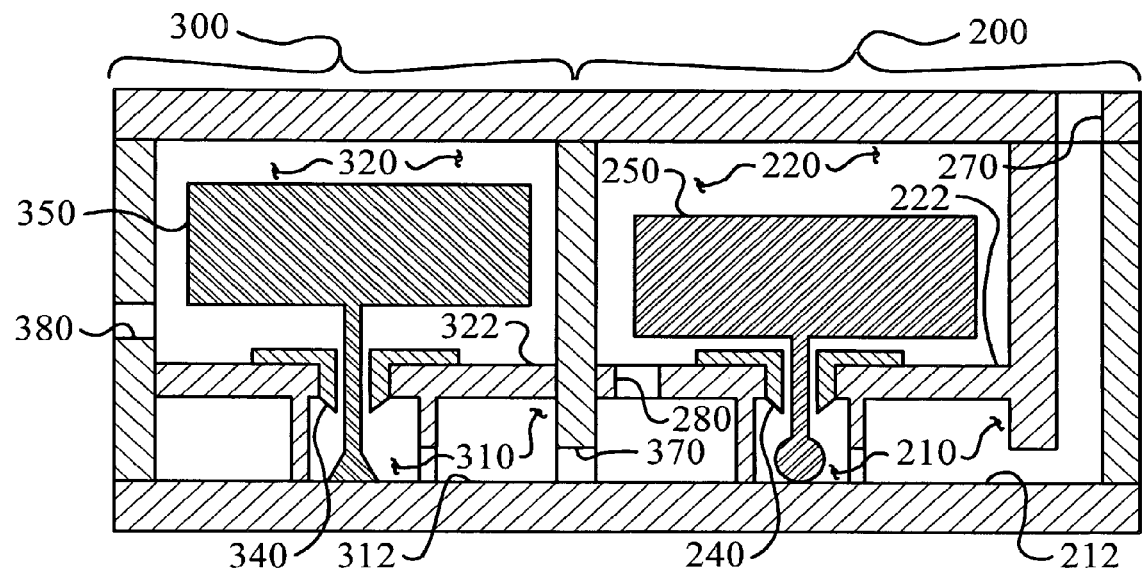
*Fig. 24*
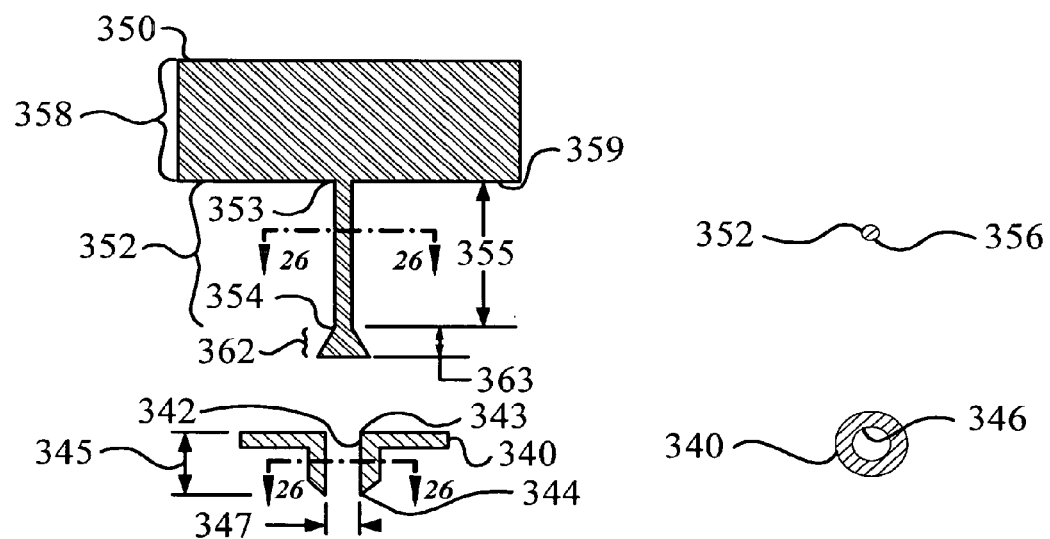
*Fig. 25*     *Fig. 26*

HEATED HUMIDIFIED CHAMBER WITH AUTOFEED MECHANISM

CROSS-REFERENCE TO RELATED APPLICATIONS

This application is a continuation of U.S. patent application Ser. No. 11/405,341, filed Apr. 17, 2006, now U.S. Pat. No. 7,614,420, issued Nov. 10, 2009, and entitled "Autofeed Mechanism for Heated Humidified Chamber"; and entire teachings of which are incorporated herein by reference.

TECHNICAL FIELD

The present disclosure generally relates to an automatic flow and level control device, especially for an autofeed mechanism particularly suited for controlling the fluid level in a heated humidifier chamber.

BACKGROUND

Automatic flow control devices have been around for hundreds, if not thousands, of years. A large portion of automatic flow control devices are dedicated to maintaining a predetermined fluid level in a reservoir, or tank. Such level maintaining automatic flow control valves have often incorporated elements that float on the surface of the fluid to indicate when the desired fluid level has been obtained. Perhaps the most famous level maintaining automatic flow control valve is that found in the storage tank of a water closet, or toilet. The water closer tank control valve includes a float mounted on a lever that is connected to a shut-off device in the water supply line. When the water in the tank rises to the desired level, the float positions the lever such that it closes the shut-off device, and accordingly the flow of water.

Such float-and-lever control devices appear relatively simple, yet as any homeowner knows, are plagued with problems. Additionally, float-and-lever control devices are not particularly well suited for miniaturization to small-scale application. Further, the level of control offered is relatively crude and not suitable for applications requiring precise level control. Still further, its reliance on an almost constantly submerged lever that must pivot in at least one location is not appropriate for critical applications. Such float-and-lever control devices are found in U.S. Pat. Nos. 3,049,144, 5,655,232, and 5,934,881.

Some automatic flow control devices have recognized the limitations imposed by the lever in the float-and-lever configuration and have incorporated an untethered float configuration. Such untethered configurations are found in U.S. Pat. Nos. 2,169,462; 2,920,644; 2,928,663; and 6,129,836. Still, many such untethered designs suffered from large size requirements and were not suitable for critical applications.

The present disclosure incorporates two free moving elements that cooperate across a seat connecting two distinct chambers. This configuration supports miniaturization of the automatic flow control device as well as robust operating capabilities, while capable of maintaining the fluid in a reservoir at a predetermined level with great precision.

SUMMARY

In some configurations, aspects of the present disclosure advance the state of the art with a variety of new capabilities and overcomes many of the shortcomings of prior devices in new and novel ways. The present disclosure overcomes the shortcomings and limitations of the prior art in any of a number of generally effective configurations. The instant disclosure demonstrates such capabilities and overcomes many of the shortcomings of prior methods in new and novel ways.

Some aspects of the present disclosure relate to a heated humidifier including a humidifier chamber and an autofeed mechanism. The autofeed mechanism is disposed within the humidifier chamber and includes a housing, a float, a stem, and a sealing body. The housing defines an inlet, an outlet, a first chamber, and a second chamber. The inlet is fluidly closed to the humidifier chamber, whereas the outlet is fluidly open to the humidifier chamber. The first chamber of the housing is fluidly connected to the inlet, whereas the second chamber is fluidly connected to the outlet. Finally, a channel is provided that fluidly connects the first and second chambers. The float is movably disposed in the second chamber. The stem projects from the float and through the channel. Finally, the sealing body is disposed within the first chamber and cooperates with the stem opposite the float. In this regard, the autofeed mechanism is configured to provide an open state and a closed state. In the open state, the sealing body is displaced from the channel to permit filling of the humidifier chamber via liquid flow from the inlet to the outlet. In the closed state, the sealing body seals the channel to prevent liquid flow from the inlet to the outlet. With this construction, a location of the sealing body relative to the channel is controlled by the float as a function of a liquid level within the humidifier chamber. Thus, the autofeed mechanism controls dispensement of liquid into the humidifier chamber as a function of the height or level of liquid within the humidifier chamber itself. In some constructions, the housing defines third and fourth chambers, with a float controlling movement of a sealing body between the third and fourth chambers providing additional control over liquid flow through the autofeed mechanism.

Yet other aspects in accordance in accordance with principles of the present disclosure relate to a method of controlling the flow of liquid into a heated humidifier chamber. An autofeed mechanism is provided within the humidifier chamber as described above. Liquid is dispensed from a source apart from the humidifier chamber into the inlet of the autofeed mechanism such that the liquid flows into the first chamber. The autofeed mechanism is operated in an open state such that the liquid fills the first chamber, rises through the channel and into the second chamber, and then is dispensed into the humidifier chamber via the outlet. In this regard, a liquid level in the humidifier chamber rises with continued dispensement of the liquid from the outlet. The autofeed mechanism is transitioned from the open state to the closed state when the liquid level in the humidifier chamber reaches a predetermined level so as to interrupt the dispensement of liquid into the humidifier chamber. To this end, the predetermined level in the humidifier chamber is transposed to the second chamber via fluid connection of the humidifier chamber and the outlet, resulting in the float buoyantly moving away from the channel to promote the sealing body sealing against the channel.

Variations, modifications, alternatives, and alterations of the various embodiments, arrangements, and configurations described herein may be used alone or in combination with one another as will become more readily apparent to those with skill in the art with reference to the following detailed description of the preferred embodiments and the accompanying figures and drawings.

BRIEF DESCRIPTION OF THE DRAWINGS

Without limiting the scope of the present disclosure as claimed below and referring now to the drawings and figures:

FIG. 1 is a partial cross sectional view of an autofeed mechanism in accordance with the present disclosure, not to scale;

FIG. 2 is an exploded assembly view of several components of the autofeed mechanism of FIG. 1, not to scale;

FIG. 3 is a cross sectional view of the primary stem portion and the primary seat, taken along section lines 3-3 in FIG. 2, not to scale;

FIG. 8 is a partial cross sectional view of an embodiment of the autofeed mechanism in accordance with the present disclosure, not to scale;

FIG. 9 is a top plan view of the primary float, not to scale;

FIG. 10 is a cross sectional view of the primary float of FIG. 9 taken along section line 10-10, not to scale;

FIG. 11 is a partial cross sectional view of an autofeed mechanism in accordance with the present disclosure, not to scale;

FIG. 12 is an exploded assembly view of several components of the autofeed mechanism of FIG. 1, not to scale;

FIG. 13 is a cross sectional view of the primary stem portion and the primary seat, taken along section lines 13-13 in FIG. 12, not to scale;

FIGS. 18-26 illustrate features of other embodiments of the present disclosure.

DETAILED DESCRIPTION

Figure 4:
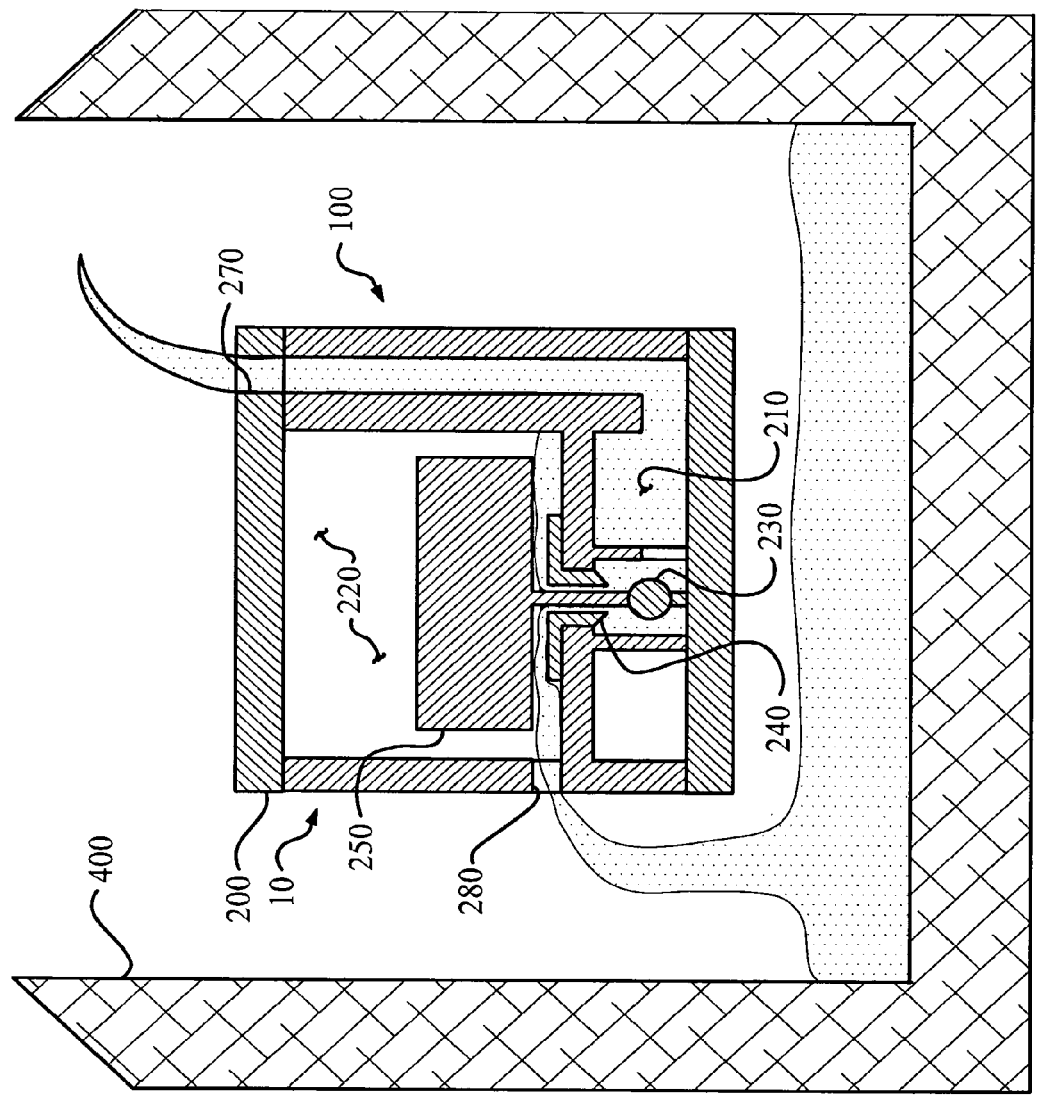
FIG. 4 is a partial cross sectional view of an embodiment of the autofeed mechanism in operation, not to scale.

The autofeed mechanism for a heated humidifier chamber 10 of the instant disclosure enables a significant advance in the state of the art. Embodiments accomplish this by new and novel arrangements of elements that are configured in unique and novel ways and which demonstrate previously unavailable but preferred and desirable capabilities. The detailed description set forth below in connection with the drawings is intended merely as a description of embodiments of the disclosure, and is not intended to represent the only form in which the present disclosure may be constructed or utilized. The description sets forth the designs, functions, means, and methods of implementing the disclosure in connection with the illustrated embodiments. It is to be understood, however, that the same or equivalent functions and features may be accomplished by different embodiments that are also intended to be encompassed within the spirit and scope of the disclosure.

Referring generally to FIGS. 1 through 17, aspects of the instant disclosure relate to an autofeed mechanism 10 for controlling the flow of a fluid to a heated humidifier chamber. It should be understood that the figures are not to scale. In fact, they are highly enlarged versions of the autofeed mechanism that would be used on a heated humidifier chamber. Further, one skilled in the art will realize that the inlets and outlets will have to be sized to allow venting of air from the chamber until the balls seat. An alternative embodiment would be to place, in the primary chamber, a hydrophobic vent. These vents are well-known to those skilled in the art and a preferred hydrophobic vent is a Gore-Tex™. that is found in the industry. The autofeed mechanism 10 includes a body 100 defining at least a primary housing 200 with a primary inlet chamber 210 and a primary float chamber 220, as seen in FIG. 1.

A primary seat 240, in cooperation with a primary float 250 and a primary ball 230, allows selective fluid communication between the primary inlet chamber 210 and the primary float chamber 220.

The basic operation of the autofeed mechanism 10 will now be briefly described, followed by a detailed disclosure of the various components of the autofeed mechanism 10. With continued reference to FIG. 1, the fluid first enters the primary fluid inlet 270, either under pressure or via gravity. The fluid then passes into the primary inlet chamber 210, where the primary ball 230 is housed. The fluid fills the primary chamber 210 and then enters the primary float chamber 220 by passing through the primary seat 240, which is partially blocked by a portion of the primary float 250. The fluid then travels laterally and exits the primary float chamber 220 via the primary fluid exit 280. The fluid generally then fills a humidifier chamber 400. This first filling of the autofeed mechanism 10 is illustrated in FIG. 4.

A few aspects of the structure of the autofeed mechanism 10 warrant review before proceeding with the sequence of operation of the mechanism 10. First, with respect to the primary inlet chamber 210, it has an inlet chamber base surface 212, seen best in FIG. 1 that may be thought of as the floor, or bottom, of the primary inlet chamber 210.

Second, with respect to the primary seat 240, best illustrated in exploded view FIG. 2, it has a primary seat channel 242 with a distal end 243 open to the primary float chamber 220 and a proximal end 244 open to the primary inlet chamber 210. The distance from the distal end 243 to the proximal end 244 defines a primary channel length 245. Additionally, the primary seat channel 242 has an opening cross sectional area 246, illustrated in FIG. 3 representing a cross sectional view of the primary seat channel 242 taken along section line 3-3 of FIG. 2.

Third, with respect to the primary float 250, it has a float portion 258, identified in FIG. 2, located in the primary float chamber 220, and a stem portion 252, also identified in FIG. 2, projecting toward the primary seat 240 and substantially parallel with the primary seat channel 242. The primary float chamber 220 is configured to allow the primary float 250 to move within the chamber 220 when acted upon by the fluid and/or the primary ball 230. Further, the stem portion 252 cooperates with the primary seat 240 so that it may move within the primary seat channel 242 with the movement of the primary float 250. The stem portion 252 has a distal end 253 at the connection to the float portion 258 and a proximal end 254 nearest the primary seat 240 with the distance between the distal end 253 and the proximal end 254 defining a stem length 255. The stem portion 252 has a stem cross sectional area 256 less than the primary seat channel opening cross sectional area 246 thereby permitting the fluid to flow through primary seat channel 242 when the stem portion 252 is in the primary seat channel 242.

Figure 6:
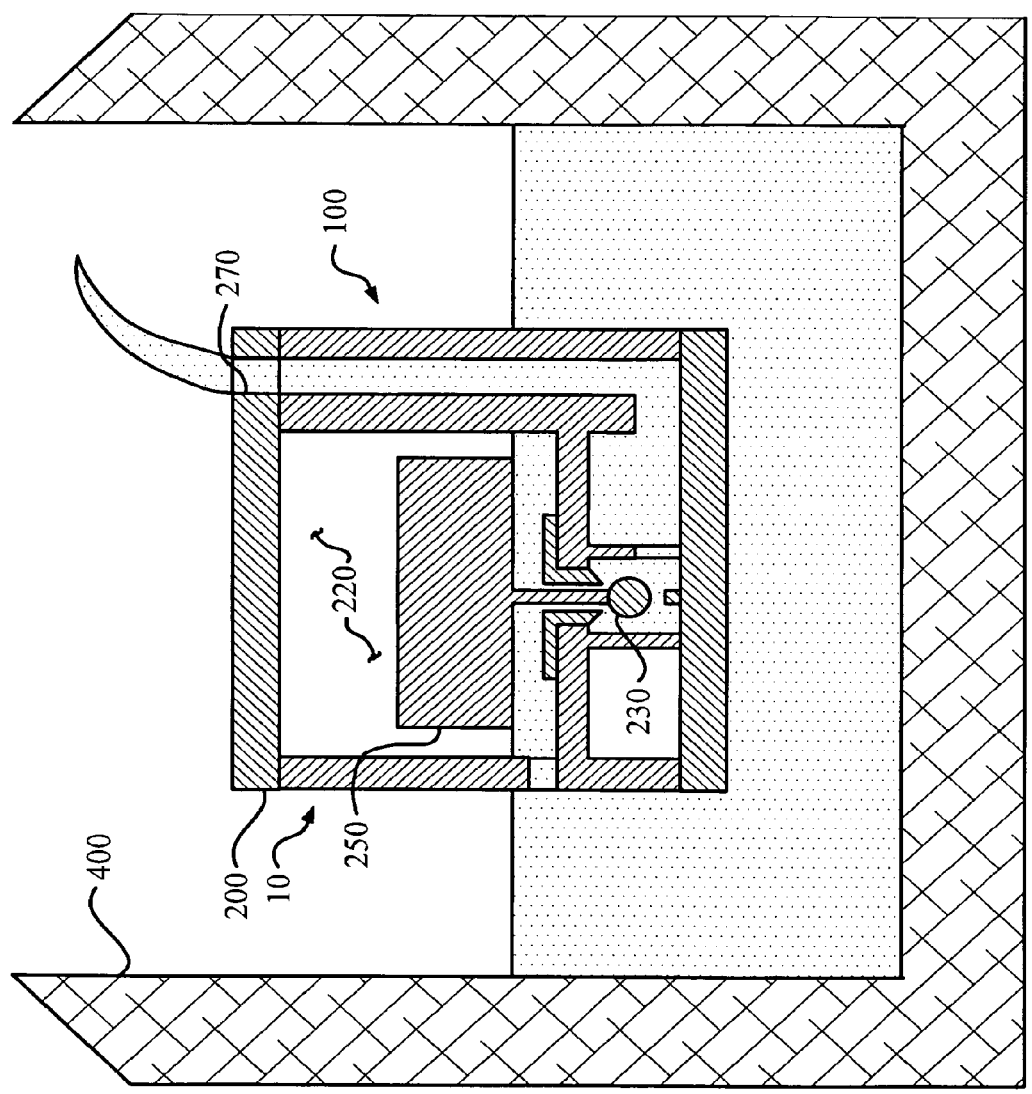
FIG. 6 is a partial cross sectional view of an embodiment of the autofeed mechanism in operation, not to scale.
Figure 7:
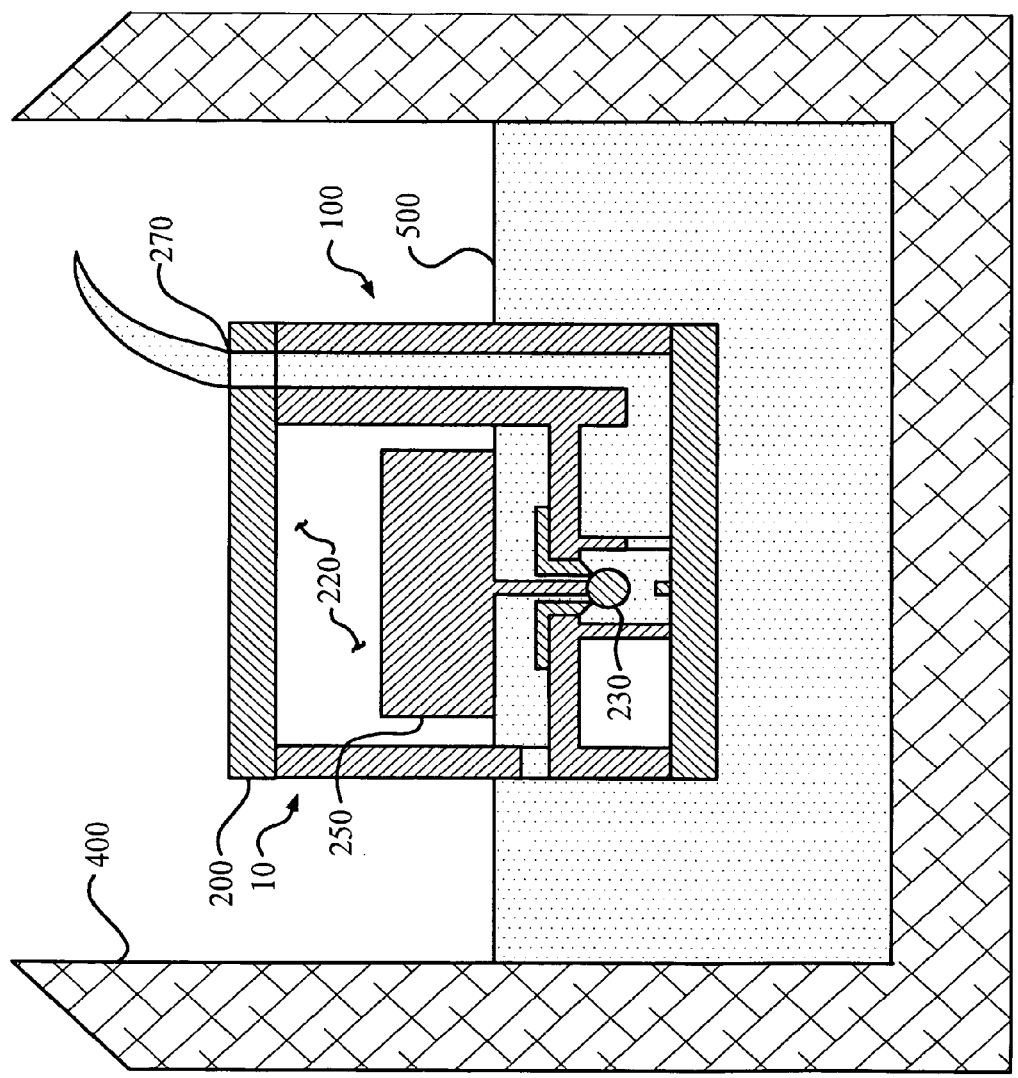
FIG. 7 is a partial cross sectional view of an embodiment of the autofeed mechanism in operation, not to scale.

Fourth, with respect to the primary ball 230, it has a diameter 232 and is located in the primary inlet chamber 210 such that the center of the primary ball 230 is substantially collinear with a central axis of the primary float stem portion 252. As previously mentioned, the primary ball 230 is acted upon by the primary float stem portion 252 thereby forcing the primary ball 230 against a ball support 214, until a predetermined fluid level is reached that begins to float the primary float 250 thereby reducing its action on the primary ball 230 and allowing the primary ball 230 to float away from the ball support 214, or the buoyant force of the primary ball 230 and the fluidic forces overtake the action of the primary float 250 causing it to move away from the primary seat 240, as seen in FIG. 6. The ball support 214 is a projection extending from the inlet chamber base surface 212 a support length 217 distance thus allowing fluid entering the primary inlet chamber 210 to pass the primary ball 230 and exit to the primary float chamber 220 and the primary fluid exit 280 by passing through the primary seat 240 around the stem portion 252. Eventually the fluid level reaches a predetermined primary fluid elevation 500 at which the action of the primary float 250 on the primary ball 230 has been reduced to the point that the primary ball 230 floats away from the ball support 214 and seals the primary seat channel proximal end 244, thereby preventing the fluid from flowing from the primary inlet chamber 210 to the primary float chamber 220 thus stopping the flow of fluid, as seen in FIG. 7.

Now, referring again to the sequence of operation, FIG. 4 illustrates the initial filling of the primary inlet chamber 210 whereby the primary float 250 is not influenced by the fluid and the weight of the primary float 250 keeps the primary ball 230 against the ball support 214 and away from the primary seat 240. As one with skill in the art will recognize, to keep the primary ball 230 against the ball support 214 the weight of the primary ball 230 must overcome the buoyant force developed due to the total submersion of the primary ball 230 and any fluidic forces.

Figure 5:
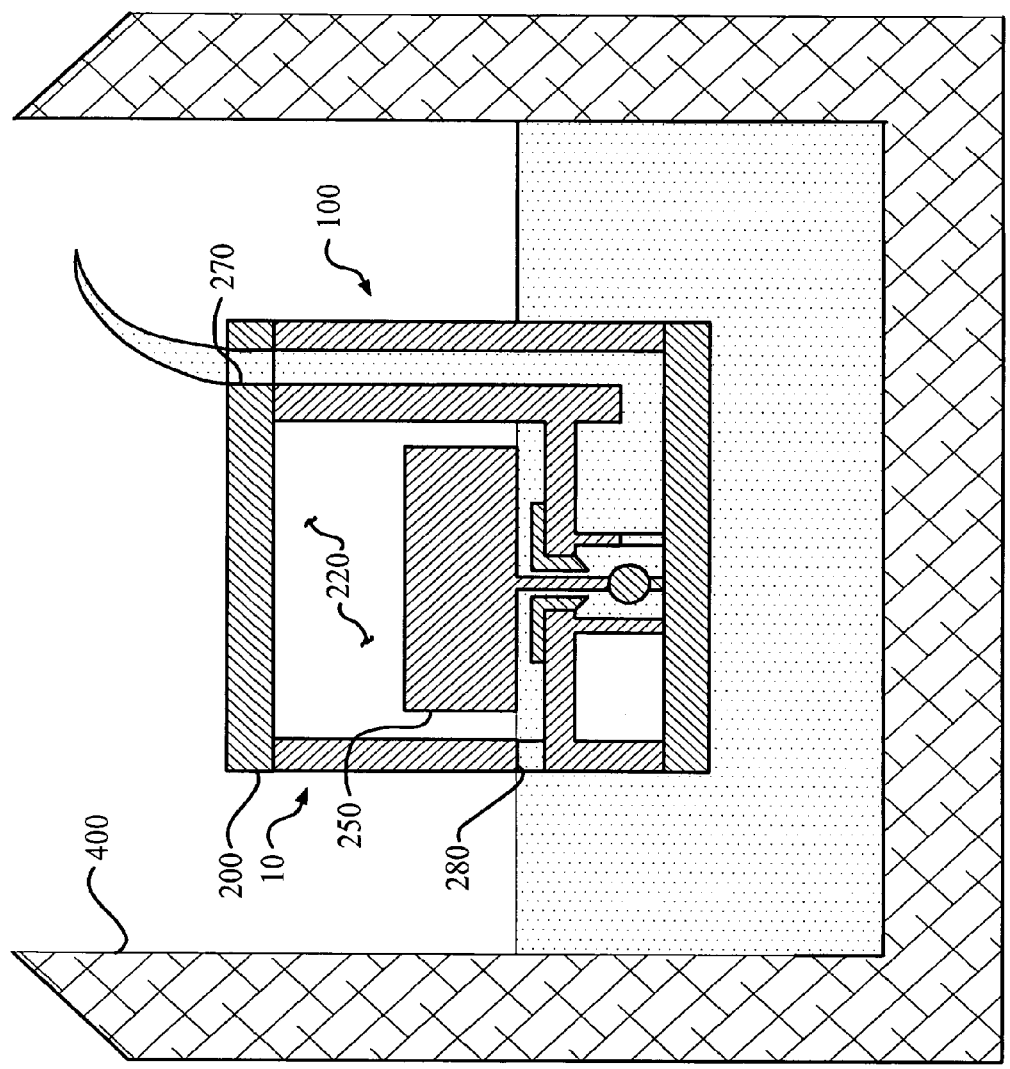
FIG. 5 is a partial cross sectional view of an embodiment of the autofeed mechanism in operation, not to scale.

Next, FIG. 5 illustrates a subsequent situation in which the fluid has now filled the primary inlet chamber 210 and the humidifier chamber 400 and the primary float chamber 220 up to the normal elevation of the float portion base surface 259, labeled in FIG. 2. Whether or not the primary float 250 begins to float at this fluid elevation depends on the construction of the primary float 250. A hollow primary float 250, or one of low density, may float at this elevation, whereas a solid primary float 250, or one of high density, may require a higher fluid elevation to begin to float. However, it is important to note that the operation of the present disclosure is not dependent upon the actual floating of the primary float 250, but rather a reduction in action on the primary ball 230 such that it may cooperate with the primary seat 240 to stop the flow of fluid. Thus, the primary float 250 functions as a counterbalance and need only counter the primary ball 230 buoyant force and any present fluidic forces. Further, the density of the primary float 250 and the primary ball 230, as well as the size and geometry of the primary float 250 and primary ball 230, may be changed to accommodate the range of elevations and pressures anticipated.

FIG. 6 illustrates the next level in which the primary ball 230 has moved away from the ball support 214 and the elevation of the primary float 250 has increased. Finally, FIG. 7 illustrates the primary ball 230 seated against the primary seat 240 thus stopping the flow of fluid and maintaining the fluid elevation at the primary predetermined fluid level 500.

Referring again to FIGS. 1 and 2, in one particular embodiment the orthogonal distance from the inlet chamber base surface 212 to the primary seat channel distal end 243 is less than the total of the support length 217, the primary ball diameter 232, and the stem length 255. This embodiment ensures the presence of a gap between the primary seat channel proximal end 244 and a float portion base surface 259 to ensure that the float portion base surface 259 does not block the primary seat channel 242 and to facilitate the flow of fluid into the primary float chamber 220. In an alternative embodiment seen in FIGS. 8, 9, and 10, the orthogonal distance from the inlet chamber base surface 212 to the primary seat channel distal end 243 is substantially equal to the total of the support length 217, the primary ball diameter 232, and the stem length 255, and a float portion base surface 259 is formed with at least one flow channel 260 to facilitate the flow of fluid from the primary seat channel 242 into the primary float chamber 220. In this embodiment, the primary float portion base surface 259 may rest directly on the primary seat 240 and not impede the fluid flow because the fluid exits the primary seat channel 242 into at least one flow channel 260 and directs the fluid to the primary float chamber 220.

Referring again to FIGS. 1 and 2, the cooperation between the primary float 250, the primary seat 240, the primary ball 230, and the ball support 214 is essential. As previously disclosed, the center of the primary ball 230 is substantially collinear with a central axis of the primary float stem portion 252. In a further embodiment, the ball support 214 is substantially collinear with the center of the primary ball 230 and with a central axis of the stem portion 252. While the ball support 214 is generally described as projecting from the primary inlet chamber base surface 212, one with skill in the art will recognize that it may equally be a recess formed in the primary inlet chamber base surface 212, or merely a tightly confined area to control the motion of the primary ball 230.

The primary float stem portion 252 is designed to be releasably received by the primary seat channel 242, yet permit the flow of fluid between the stem portion 252 and the seat channel 242. Therefore, the stem cross sectional area 256 must be less than the primary seat channel opening cross sectional area 246, as seen in FIG. 3. In one particular embodiment, the stem cross sectional area 256 is at least ten percent less than the primary seat channel opening cross sectional area 246.

Further, the primary seat channel distal end 244 must be configured to cooperate with the primary ball 230 to ensure that the primary ball 230 creates a liquid-tight seal against the primary seat 240. As such, in one particular embodiment the primary seat channel opening cross sectional area 246 at the primary seat channel proximal end 244 is at least ten percent less than the maximum cross sectional area of the primary ball 230. One with skill in the art will appreciate that despite the use of the word "ball," the primary ball 230 need not be spherical in shape, in fact, it may be any object that will create a seal against the primary seat 240 and can be displaced by the primary float 250. In fact, the primary ball 230 may be virtually any geometric shape, including, but not limited to, a conical shape or a flat shape such as a film or disk.

Now, with the embodiments of FIGS. 1-10 disclosed, a dual housing embodiment will be disclosed. Referring generally to FIGS. 11 through 17, the instant embodiment incorporates a second autofeed system to introduce a redundancy, or fail-safe, into the autofeed mechanism 10 of the present disclosure. In this embodiment the autofeed mechanism 10 includes a body 100 defining a primary housing 200 and a secondary housing 300. The elements of the secondary housing 300 are substantially identical to those of the primary housing 200, only now with reference numerals in the 300's rather than the 200's, and incorporating reference to "secondary" in the element description, rather than the references to "primary" associated with the elements of the primary housing 200. Therefore, the prior disclosure with respect to the primary housing 200 will not be repeated here, it is incorporated by reference with respect to FIGS. 11, 12, and 13, in lieu of FIGS. 1, 2, and 3, and the secondary housing 300 elements.

The setup of the secondary housing 300 may be identical to the primary housing 200 with the elevation of the primary float chamber base surface 222 equal to that of the secondary float chamber base surface 322, however it is preferred to have the housings 200, 300 setup to alert an observer of a failure in the primary housing 200. Therefore, as seen in FIGS. 11 and 12, the secondary float chamber base surface 322 is higher in elevation than the primary float chamber base surface 222 and the secondary ball support length 317 is greater than the primary ball support length 217 thus establishing a secondary fluid level 600 that is higher in elevation than the primary fluid level 500, thereby providing a visual indication that the components of the primary housing 200 are not properly functioning. In this embodiment, the primary fluid exit 280 is in fluid communication with the secondary fluid inlet 370. A failed primary float can be indicated by an elevated water level that is established by raising the base of the secondary float chamber. The elevated water level can also be established by changing the configuration of the secondary float. This will change the affect on the buoyancy and therefore delay the elevation of the secondary float leading to higher water level in the chamber. Since the design of this autofeed places a ball in the direct flow path upstream to the seat, the design is resistant to leakage due to elevated water levels in the feed bag. In other words, in the typical design the higher the water bag, the more water pressure on the seat and the greater the chance of dislodging the mechanism that seals the seat. With this design, the higher water pressure actually does the opposite and forces the ball further onto the seat. This will result in the humidifier chamber not getting water, but it will also ensure that the patient does not get drowned by the water in the bag.

Figure 14:
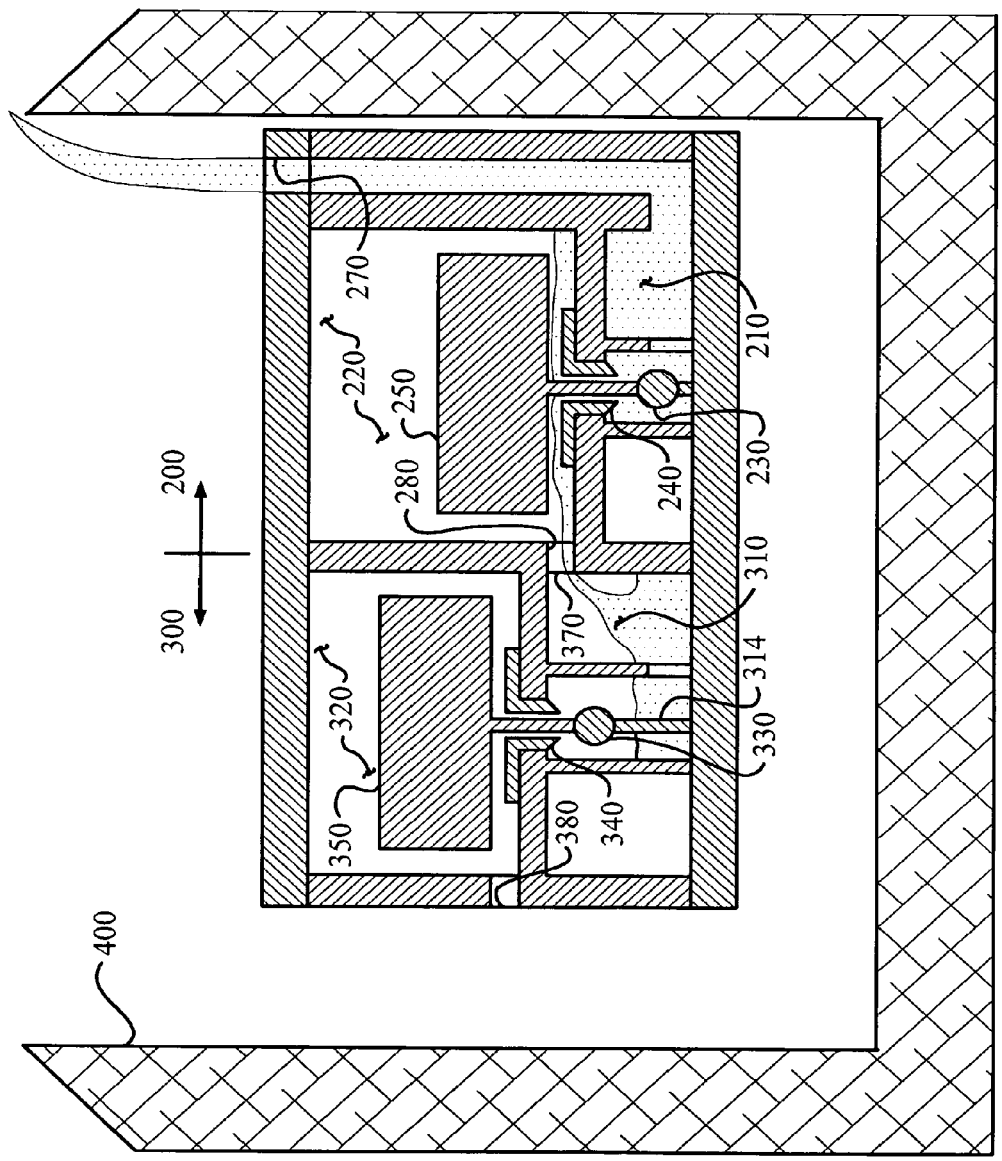
FIG. 14 is a partial cross sectional view of an embodiment of the autofeed mechanism in operation, not to scale.

Now, referring to the sequence of operation, FIG. 14 illustrates the initial filling of the primary inlet chamber 210 and the secondary inlet chamber 310 whereby the primary float 250 and the secondary float 350 are not influenced by the fluid and the weight of the primary float 250 keeps the primary ball 230 against the primary ball support 214 and away from the primary seat 240 and the weight of the secondary float 350 keeps the secondary ball 330 against the secondary ball support 314 and away from the secondary seat 340. As one with skill in the art will recognize, to keep the primary ball 230 against the ball support 214 the weight of the primary ball 230 must overcome the buoyant force developed due to the total submersion of the primary ball 230 and any fluidic forces.

Figure 15:
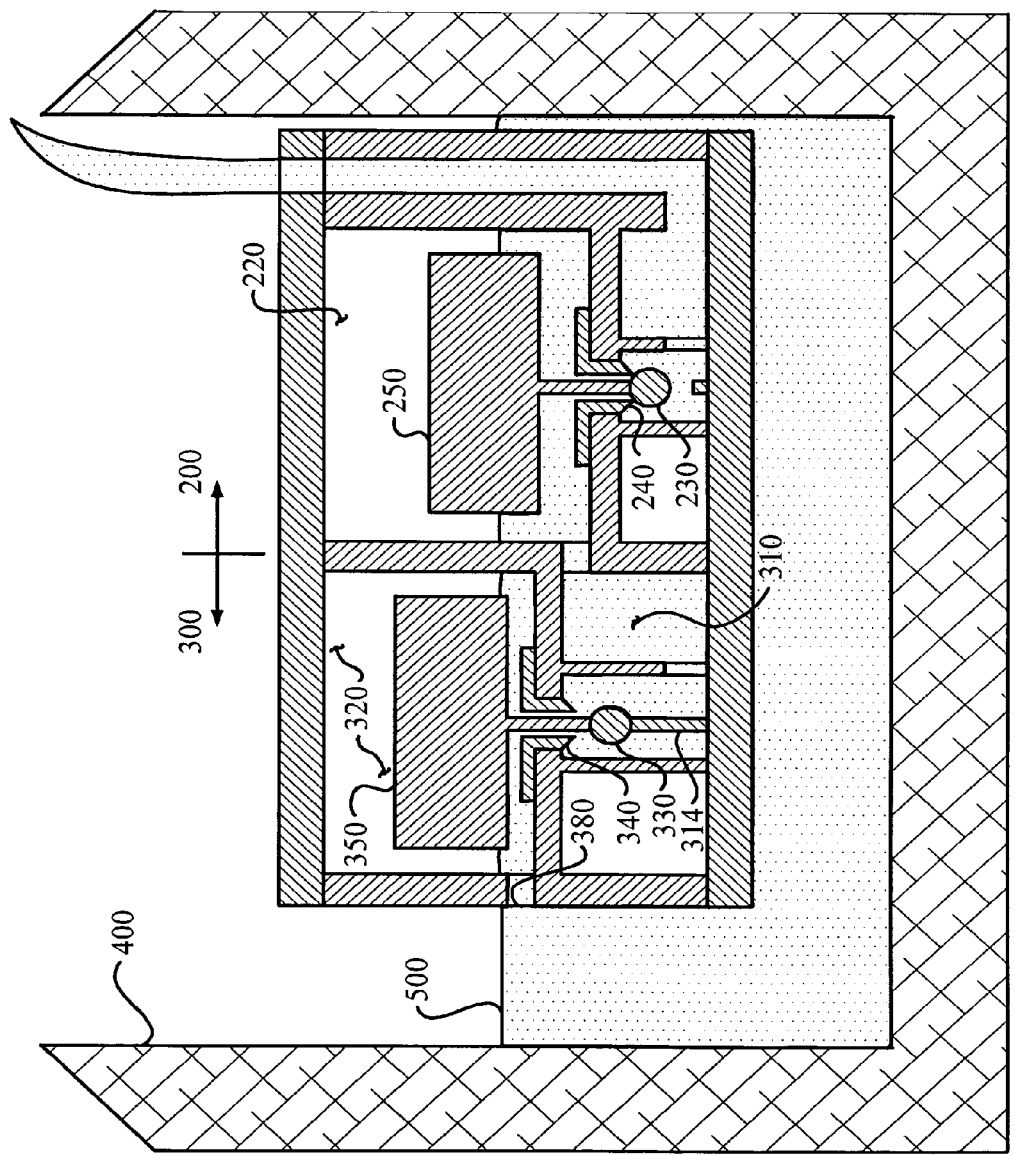
FIG. 15 is a partial cross sectional view of an embodiment of the autofeed mechanism in operation, not to scale.

Next, FIG. 15 illustrates the situation in which the components of the primary housing 200 function properly and the primary ball 230 stops the flow of fluid through the primary seat 240, thus maintaining the primary fluid level 500. In this situation, the fluid level has not increased enough to reduce the action of the secondary float 350 on the secondary ball 330 to the point that the secondary ball 330 leaves the secondary ball support 314.

Figure 16:
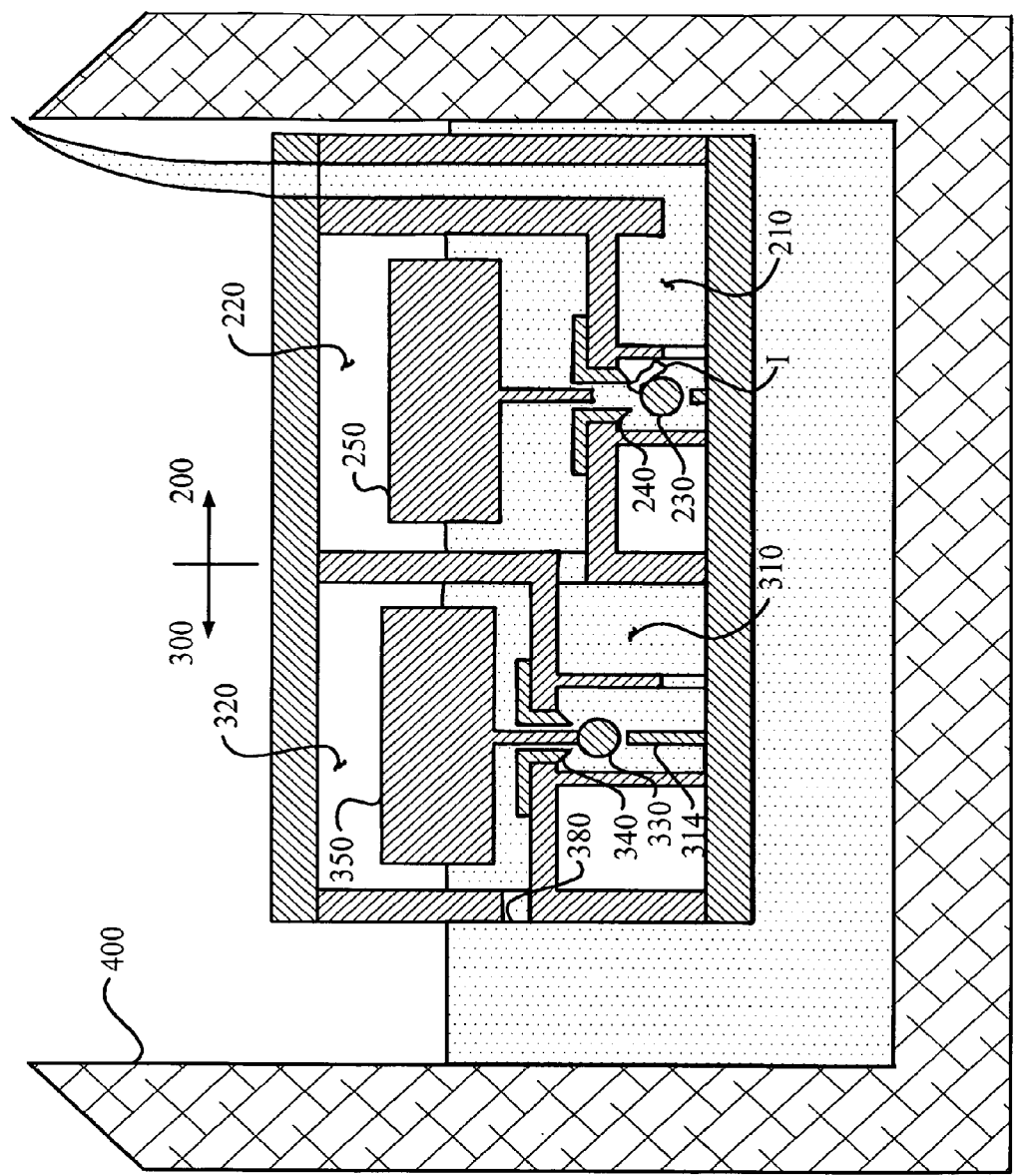
FIG. 16 is a partial cross sectional view of an embodiment of the autofeed mechanism in operation, not to scale.
Figure 17:
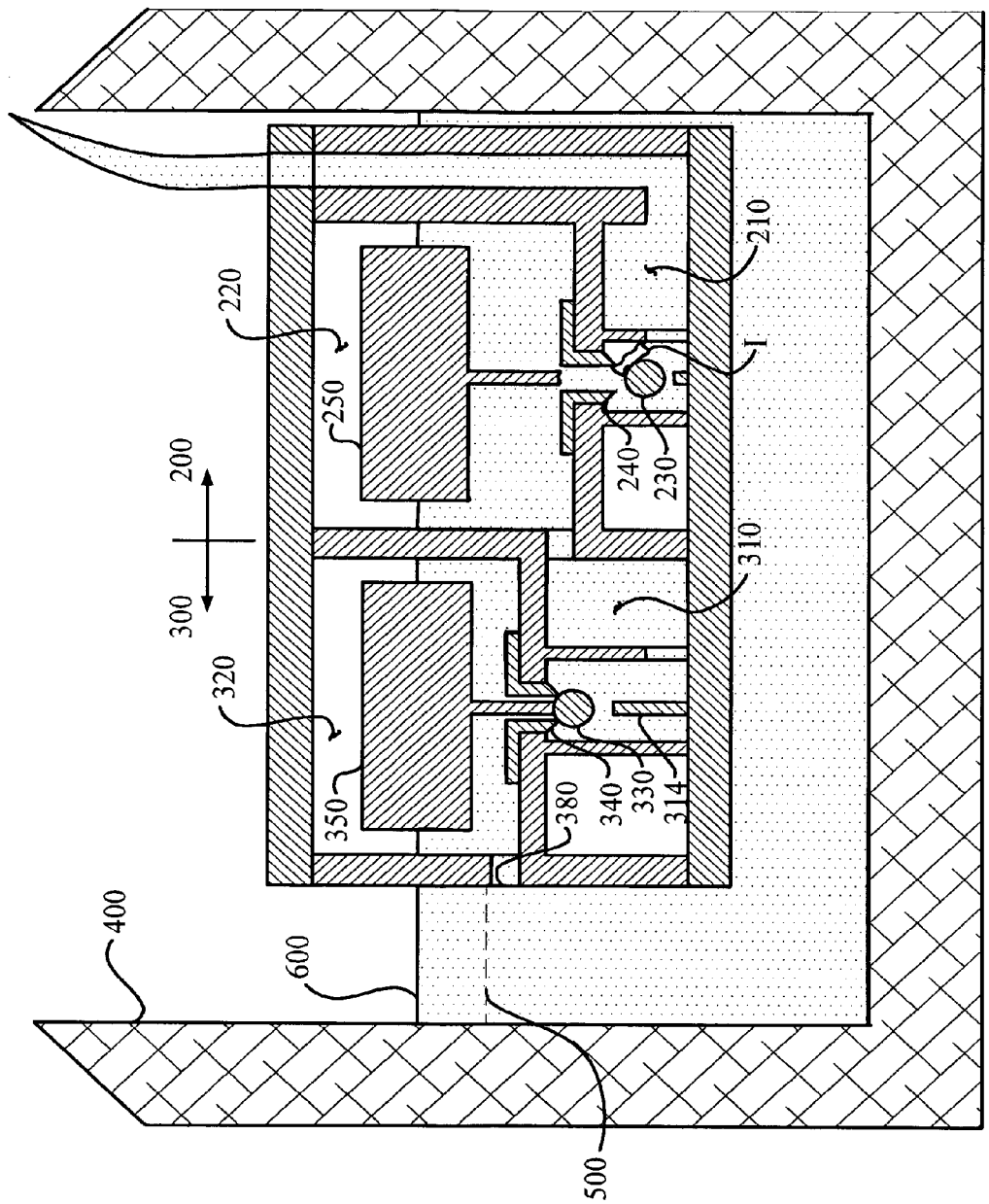
FIG. 17 is a partial cross sectional view of an embodiment of the autofeed mechanism in operation, not to scale.
Figure 18:
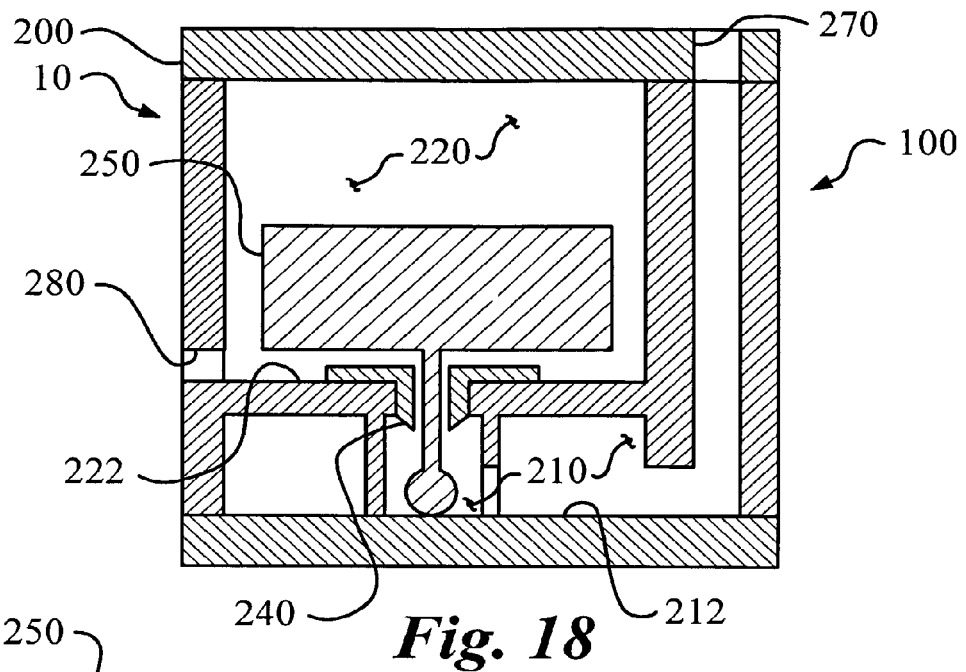
Figures 19, 20:
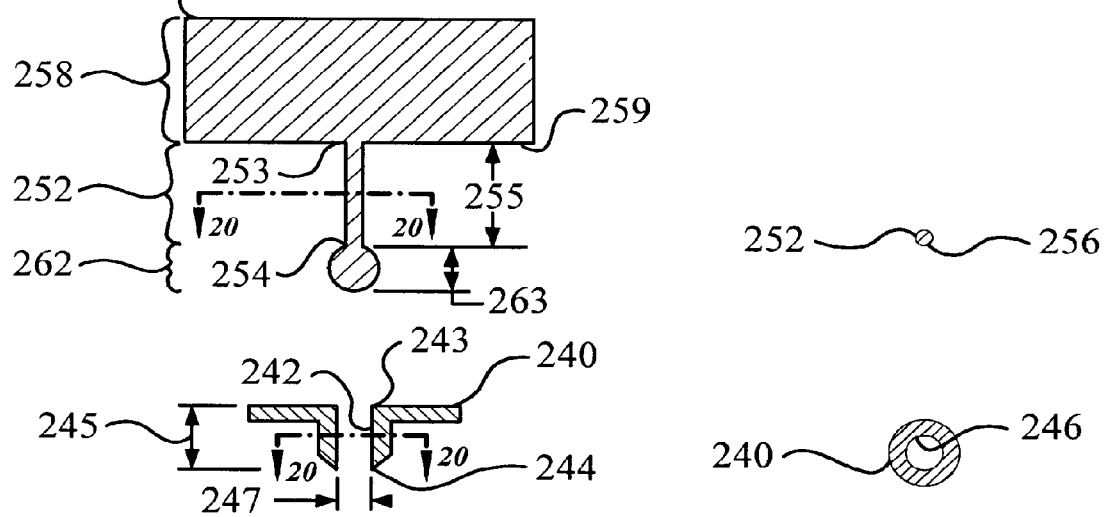

FIG. 16 illustrates a situation in which an impediment I is lodged between the primary ball 230 and the primary seat 240, thus preventing the primary ball 230 from sealing against the primary seat 240. In such a situation, the fluid level would continue to rise in an uncontrolled manner if not for the presence of the secondary housing 300. Here, the fluid level rises until the force exerted on the secondary ball 330 by the secondary float 350 is reduced to the point that it is overcome by the buoyant force of the secondary ball 330 resulting in the secondary ball 330 leaving the secondary ball support 314, as seen in FIG. 16. Eventually the secondary ball 330 closes the secondary seat channel proximal end 344 once the fluid level has reached the secondary fluid level 600. The difference in elevation between the secondary fluid level 600 and the primary fluid level 500, seen in FIG. 17, provides an indication to the operator that the autofeed mechanism 10 is not properly functioning and requires service. Any number of audio, visual, and tactile alarm indicators may be incorporated into the autofeed mechanism 10 to sense the change in normal fluid level and warn of malfunctions.

One with skill in the art will recognize that the humidifier chamber 400 illustrated in the accompanying figures is merely schematic in nature. Further, the autofeed mechanism 10 and its components may be fabricated from a wide variety of materials, selected to reflect particular characteristic desired for operation with a variety of fluids, including, by way of example and not limitation, metals, plastic, glass, natural and synthetic rubbers, and composites of various types.

Numerous alterations, modifications, and variations of the preferred embodiments disclosed herein will be apparent to those skilled in the art and they are all anticipated and contemplated to be within the spirit and scope of the instant disclosure. For example, although specific embodiments have been described in detail, those with skill in the art will understand that the preceding embodiments and variations can be modified to incorporate various types of substitute and or additional or alternative materials, relative arrangement of elements, and dimensional configurations. Accordingly, even though only few variations of the present disclosure are described herein, it is to be understood that the practice of such additional modifications and variations and the equivalents thereof, are within the spirit and scope of the disclosure as defined in the following claims.

Although the present disclosure has been described with reference to preferred embodiments, workers skilled in the art will recognize that changes can be made in form and detail without departing from the spirit and scope of the present disclosure.

INDUSTRIAL APPLICABILITY

The autofeed mechanism for a heated humidifier chamber answers a long felt need for a novel flow control device that eliminates the problems commonly associated with lever actuated flow control systems. The mechanism is easy to manufacture and assemble due, in part, to the low number of moving components. The simple construction results in a significant advance over prior art autofeed devices. Further, the various components of the present disclosure are easily changed out to adjust the operating parameters of the mechanism, a feature lacking from the prior art.

What is claimed is:
1. A heated humidifier comprising:
a humidifier chamber; and
an autofeed mechanism disposed within the humidifier chamber, the autofeed mechanism including:
a housing defining:
an inlet,
an outlet,
wherein the inlet is fluidly closed to the humidifier chamber and the outlet is fluidly open to the humidifier chamber,
a first chamber fluidly connected to the inlet,
a second chamber fluidly connected to the outlet,
a channel fluidly connecting the first and second chambers;
a float movably disposed in the second chamber,
a stem projecting from the float and through the channel, a sealing body disposed within the first chamber and cooperating with the stem opposite the float, wherein the sealing body is detached from the stem;

wherein the autofeed mechanism is configured to provide an open state in which the sealing body is displaced from the channel to permit filling of the humidifier chamber via liquid flow from the inlet to the outlet, and a closed state in which the sealing body seals the channel to prevent liquid flow from the inlet to the outlet;

and further wherein a location of the sealing body relative to the channel is controlled by the float as a function of a liquid level within the humidifier chamber;

and further wherein a buoyancy of the float and the sealing body in water is such that transitioning of the sealing body from a lower-most vertical location relative to the first chamber to the closed state occurs solely due to the buoyant force of the sealing body in water.

2. The heated humidifier of claim 1, wherein the sealing body is cylindrical.

3. The heated humidifier of claim 1, wherein the sealing body is conical.

4. The heated humidifier of claim 1, wherein the sealing body is a disk-like body.

5. The heated humidifier of claim 1, wherein the stem has a width smaller than a width of the float and a width of the sealing body.

6. The heated humidifier of claim 1, further comprising a seat disposed in the second chamber and protruding through the channel, the stem being slidably disposed within the seat.

7. The heated humidifier of claim 6, wherein the seat is removably secured within the channel.

8. The heated humidifier of claim 1, wherein a lower-most floor of the first chamber is disposed below a lower-most bottom of the second chamber.

9. The heated humidifier of claim 1, further comprising a sealing body support fixed to a bottom surface of the housing and directly opposite the channel.

10. The heated humidifier of claim 1, wherein the housing includes a removable exterior section configured to facilitate removal and replacement of the float.

11. The heated humidifier of claim 1, wherein inlet is vertically above the outlet.

12. The heated humidifier of claim 1, wherein the autofeed mechanism further includes:
a third chamber formed by the housing, fluidly between the inlet and the first chamber, the third chamber being fluidly open to the inlet;
a fourth chamber formed by the housing, fluidly between the third chamber and the first chamber, the fourth chamber being fluidly open to the first chamber;
a second channel fluidly connecting the third and fourth chambers;
a second float movably disposed in the fourth chamber;
a second stem projecting from the second float and through the second channel;
a second sealing body disposed within the third chamber and cooperating with the second stem opposite the second float;
wherein the open state of the autofeed mechanism further includes the second sealing body displaced from the second channel to permit liquid flow from the inlet to the first chamber.

13. The heated humidifier of claim 12, wherein the autofeed mechanism is configured to alert an observer as to a failure of one of the sealing bodies.

14. The heated humidifier of claim 1, wherein the autofeed mechanism housing is fluidly disposed within the humidification chamber.

15. The heated humidifier of claim 1, further comprising a sealing body support, wherein in the open state the sealing body is disposed on the sealing body support.

16. The heated humidifier of claim 1, wherein the float has a first buoyancy and the sealing body has a second buoyancy, the first buoyancy differing from the second buoyancy.

17. The heated humidifier of claim 1, wherein the stem forms a first end attached to the float and terminates at a second end opposite the first end, and further wherein contact between the stem and the sealing body in any state of the autofeed mechanism is limited to an abutting interface between the second end and the sealing body.

18. The heated humidifier of claim 1, wherein the stem forms a first end attached to the float and terminates at a second end opposite the float, and further wherein an entirety of the stem is vertically above the sealing body.

19. A heated humidifier comprising:
a humidifier chamber; and
an autofeed mechanism disposed within the humidifier chamber, the autofeed mechanism including:
a housing defining:
an inlet,
an outlet,
wherein the inlet is fluidly closed to the humidifier chamber and the outlet is fluidly open to the humidifier chamber,
a first chamber fluidly connected to the inlet,
a second chamber fluidly connected to the outlet,
a channel fluidly connecting the first and second chambers;
a float movably disposed in the second chamber,
a stem projecting from the float and through the channel,
a sealing body disposed within the first chamber and cooperating with the stem opposite the float;
wherein the autofeed mechanism is configured to provide an open state in which the sealing body is displaced from the channel to permit filling of the humidifier chamber via liquid flow from the inlet to the outlet, and a closed state in which the sealing body seals the channel to prevent liquid flow from the inlet to the outlet;
wherein a location of the sealing body relative to the channel is controlled by the float as a function of a liquid level within the humidifier chamber;
and further wherein the second chamber is defined by a floor through which the channel extends, and further wherein the float includes a major surface facing the floor, the major surface defining a plurality of flow grooves configured to permit fluid flow through the channel and into the second chamber when the major surface is in contact with the floor.

20. The heated humidifier of claim 19, wherein the float, the stem, and the sealing body are integrally formed.

21. A method of controlling the flow of liquid into a heated humidifier chamber, the method comprising:
receiving a heated humidifier including an autofeed mechanism within a humidifier chamber, the autofeed mechanism including:
a housing defining an inlet, an outlet, a first chamber, and a second chamber, the first chamber being fluidly connected to the inlet, the second chamber being fluidly connected to the outlet, and a channel fluidly connecting the first and second chambers, wherein the second chamber is defined by a floor through which the channel extends, a float moveably disposed within the second chamber, wherein the float includes a major surface facing the floor, a stem extending from the float and through the channel, a sealing body disposed within the first chamber and cooperating with the stem opposite the float, wherein the autofeed mechanism is operable in an open state in which the sealing body is displaced from the channel, and a closed state in which the sealing body closes the channel;

dispensing liquid for delivery to a patient from a source apart from the humidifier chamber into the inlet such that the liquid flows into the first chamber, wherein prior to initial dispensing of liquid into the first chamber, the sealing body is in a lower-most vertical position relative to the first chamber;

operating the autofeed mechanism in the open state such that the liquid fills the first chamber, rises through the channel and into the second chamber, and then is dispensed into the humidifier chamber via the outlet;

wherein a liquid level in the humidifier chamber rises with continued dispensement of the liquid from the outlet;

transitioning the autofeed mechanism from the open state to the closed state when the liquid level in the humidifier chamber reaches a pre-determined level, the pre-determined level being transposed to the second chamber via fluid connection of the humidifier chamber and the outlet, resulting in the float buoyantly rising away from the channel and the sealing body simultaneously buoyantly rising toward the channel and sealing against the channel, wherein an entirety of the rising movement of the sealing body from the lower-most vertical position occurs without an upward force being applied to the sealing body by the float; and transitioning the autofeed mechanism from the closed state to the open state when the liquid level in the second chamber lowers as liquid is dispensed from the outlet, and not the inlet, resulting in the float buoyantly moving toward the channel to promote the sealing body cooperating with the stem to release the sealing body from the channel.

22. The method of claim 21, wherein the major surface of the float defines a plurality of flow grooves configured to permit liquid flow through the channel and into the second chamber when the major surface is in contact with the floor in the open state of the autofeed mechanism.

* * * * *

UNITED STATES PATENT AND TRADEMARK OFFICE
CERTIFICATE OF CORRECTION

PATENT NO. : 8,033,292 B2
APPLICATION NO. : 12/607277
DATED : October 11, 2011
INVENTOR(S) : Andre Rustad et al.

It is certified that error appears in the above-identified patent and that said Letters Patent is hereby corrected as shown below:

Column 4, line 9, after "Gor-Tex™" please delete ".".

Column 4, line 9, after "FIG. 1." please insert -- A primary seat 240, in cooperation with a primary float 250 and a primary ball 230, allows selective fluid communication between the primary inlet chamber 210 and the primary float chamber 220. --.

Column 4, lines 10-13, please delete "A primary seat 240, in cooperation with a primary float 250 and a primary ball 230, allows selective fluid communication between the primary inlet chamber 210 and the primary float chamber 220.".

Signed and Sealed this
Twenty-fourth Day of April, 2012

David J. Kappos
*Director of the United States Patent and Trademark Office*